United States Patent [19]

Yolles

[11] 4,283,342

[45] Aug. 11, 1981

[54] ANTICANCER AGENTS AND METHODS OF MANUFACTURE

[75] Inventor: Seymour Yolles, Newark, Del.

[73] Assignee: University of Delaware, Newark, Del.

[21] Appl. No.: 117,378

[22] Filed: Jan. 31, 1980

[51] Int. Cl.³ ............... C07D 309/00; C07D 311/00; C07F 15/00

[52] U.S. Cl. ............... 260/345.1; 260/366; 260/429 R

[58] Field of Search ............... 260/429 R, 366, 345.1

[56] References Cited

U.S. PATENT DOCUMENTS

| 2,895,967 | 7/1959 | Straley et al. | 260/366 |
|---|---|---|---|
| 3,192,236 | 6/1965 | O'Connell | 260/366 |
| 4,169,846 | 10/1979 | Kidani et al. | 260/429 R |
| 4,200,583 | 4/1980 | Kidami et al. | 260/429 R X |

OTHER PUBLICATIONS

Yolles et al., Acta Pharmaceutica Suecia, 15, 382–388 (1978).
Chemical Abstracts, 89 99746v (1978).
Chemical Abstracts, 85 28554n (1976).
Chemical Abstracts, 84 31164v (1976).

*Primary Examiner*—Helen M. S. Sneed

[57] ABSTRACT

A therapeutic metal coordination compound, particularly useful as an anticancer agent, which is the reaction product of a hydroxy quinone and a cisplatinum (II) compound substituted with chloro ligands and ammonia or derivatized ammonia ligands and the process for its manufacture.

9 Claims, No Drawings

ANTICANCER AGENTS AND METHODS OF MANUFACTURE

BACKGROUND OF THE INVENTION

In previous work [Acta Pharmaceutica, Suecica, 15, 382–388 (1978), published February 1, 1979] applicant S. Yolles and co-workers V. Morton and B. Rosenberg reported that composites of cis dichlorodiammineplatinum(II), abbreviated cis-Pta$_2$Cl$_2$, with doxorubicin and cyclophosphamide in poly (lactic acid), (PLA), showed a substantial and unexpected improvement in the life span of mice, in comparison with composites containing only cis-Pta$_2$Cl$_2$. Specifically, 64 mg of composite cis-Pta$_2$Cl$_2$ -doxorubicin-cyclophamide per kg mouse could be tolerated whereas cis-Pta$_2$Cl$_2$ is toxic at 7 mg/kg mouse.

This work was covered by U.S. application Ser. No. 859,766 filed Dec. 12, 1977, for "Controlled Release of Anticancer Agents from Biodegradable Polymers" in the name of Seymour Yolles.

Complexes of 5,8-dihydroxy-1,4 naphthoquinone with several metals (beryllium, cobalt, copper, nickel and zinc) have been reported and their thermal stabilities determined [refer R. S. Bottei and P. L. Gerace, *J. Inorg. Nucl. Chem.*, 23, 245, (1961)]. This study reported an unsuccessful attempt to prepare a platinum metal compound with 5,8-dihydroxy-1,4-napthoquinone.

H. D. Coble and H. F. Holtzclaw, Jr., *J. Inorg. Nucl. Chem.*, 36, 1049 (1974) reported the properties of chelate polymers of copper (II) with several hydroxyquinones, including 5,8-dihydroxy-1,4 napthoquinone, 1,4-dihydroxy-and 1,5-dihydroxy-9,10 anthraquinone and 6,11-dihydroxy naphthacenequinone.

More recently, C. G. Pierpont, L. C. Francesconi and D. M. Hendrickson, *Inorg. Chem.* 17, 3470 (1978) reported preparation and characterization of binuclear nickel (II) and copper (II) complexes bridged by the dianions of 5,8-dihydroxy-1,4-naphthoquinone, and 1,4-dihydroxy-and 1,5 dihydroxy-9,10 anthraquinones.

S. Cenini, R. Ugo and G. Lamonica, *Jl. Chem. Soc* [A], 1971, p. 416 reported the preparation of two different chelates, with benzoquinone, one being of the 2-olefinic type and the other an orthoquinone, by reaction with diphosphine PtCl$_2$ (O).

M. Gonsalves, et al, *Europ. J. Cancer*, Vol. 14, p. 1185 (1978) discloses the preparation and therapeutic advantages of "Ouelamycin," a complex of doxorubicin (Adriamycin ®) with iron having the formula:

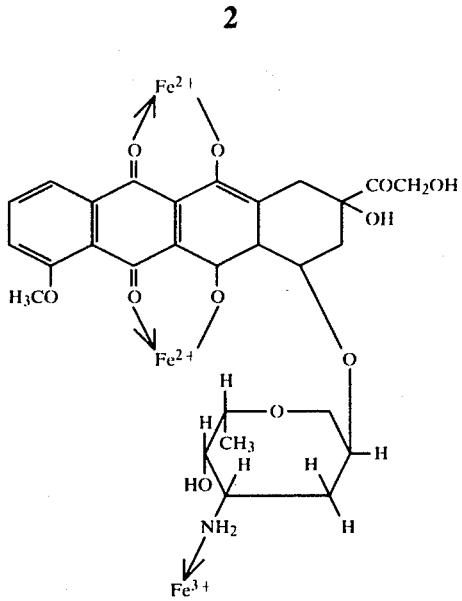

Finally, the September, 1979, Am. Chem. Soc, Inorganic Abstracts, Abstract 169, of Papers advises that F. T. Greenaway and J. C. Dabrowiak studied the metal-binding properties of doxorubicin and the chemically related compound, daunomycin, for Cu (II), Zn (II), Mg (II), Co (II), Ni (II) and Fe (III) ions.

According to the spectroscopic data, the metals bind to the aglycone and, at least in the case of Cu (II), to the amine function of daunosamine.

The distinction between daunomycin and doxorubicin is seen from the following structural formula:

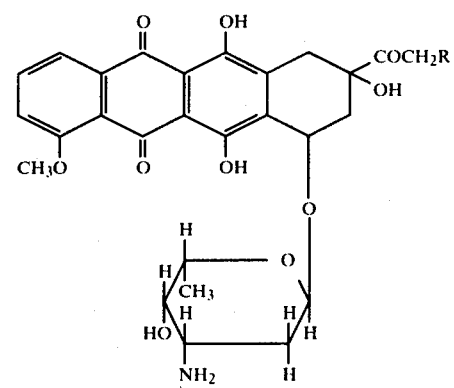

wherein R=H for daunomycin and R=OH for doxorubin

SUMMARY OF THE INVENTION

This invention relates broadly to a metal coordination compound comprising, as a therapeutic portion,
(a) a multi-ring quinone having at least one hydroxy group in a ring fused to the quinone ring as ligand,
(b) chelated at keto and hydroxy groups with the platinum metal
(c) in a cis-dichloro platinum (II) compound having two platinum metal coordinate bonds each joined to a member of the group consisting of ammonia, mono-substituted ammonia and ammonia radicals connected one to the other by simple valence bonds through adjacent carbons of a carbon ring compound, and (d) additional cis-dichloro platinum (II) compound not bonded to the hydroxy quinone but coordinated to said platinum which is bonded to said hydroxy quinone, and, as a non-therapeutic portion,
(e) excess platinum in the form of tetrachloroplatinate anion, together with the method of manufacturing such compounds.

DETAILED DESCRIPTION OF THE INVENTION

The anticancer properties of cis-dichlorodiammineplatinum (II), abbreviated cis-Pta$_2$Cl$_2$, are well known, as are also the anticancer properties of doxorubicin. However, cis-Pta$_2$Cl$_2$ is relatively toxic, and the release rates of Pta$_2$Cl$_2$ and doxorubicin, as individual components of mixtures, such as taught in U.S. Application Ser. No. 859,766 supra, can possibly vary independently one from the other in different utilization environments, contributing to a loss of sustained dosage control.

I have now found that it is possible to prepare platinum metal coordination compounds of multi-ring quinones having at least one hydroxy group in a ring fused to the quinone ring as ligand, which definition also includes doxorubicin specifically.

Surprisingly, these metal coordination compounds, specifically the compound doxorubicin with cis-dichlorodiammine platinum (II), displays a synergistic increase in anticancer activity as compared with doxorubicin, cis-Pta$_2$Cl$_2$ (II) mixtures per se. In addition, metal coordination with a number of other hydroxysubstituted quinones hereinafter described provides completely new anticancer agents not heretofore available.

The preparation of metal coordination compounds according to this invention cannot be effected by the usual techniques but, instead, requires prolonged special ball milling of mixtures of the specific hydroxy-substituted multi-ring quinones with the cis-dichloro diammonia type platinum (II) compound in the presence of a liquid heat sink, preferably a solvent for at least one of the ingredients. Ball milling must be conducted in ceramic or glass jars using glass, ceramic or other non-metallic balls, the progress of coordination complexing being indicated by the gradual development of an intense purple coloration of the reaction mixture.

Using quinizarin as example (refer Example 3 infra) it is postulated that the dihydroxy quinone metal coordination compounds according to this invention have the following general structure, the therapeutic portion being bracketed whereas the non-therapeutic portion is represented by the tetrachloroplatinate anion shown to the right. The compound illustrated has a Pta$_2$Cl$_2$ to quinone ratio of 11 to 2 which agrees, within limits of experimental error, with the analyses made for identified Examples infra.

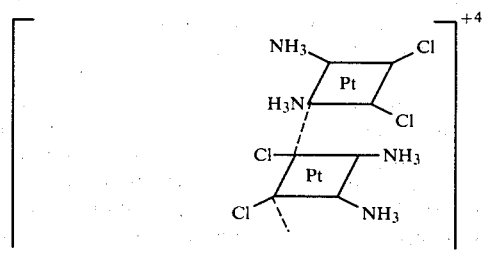

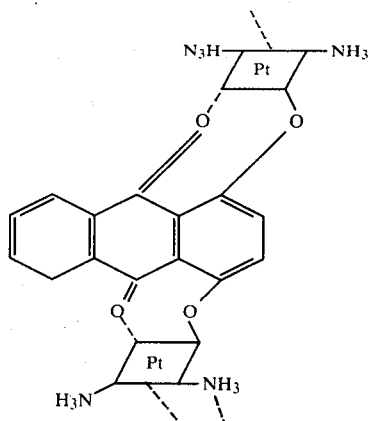
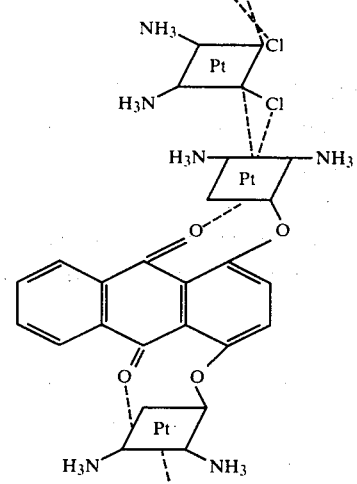
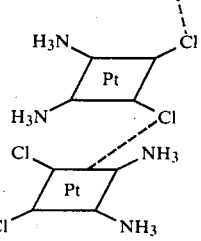

The foregoing postulated structure is confirmed by the stoichiometric analyses assumed and actually conducted for the several Examples hereinafter described. Thus, in Examples 2, 3 and 4, the molar ratio of cis Pta$_2$Cl$_2$ to quinone approximates 5:1 or 6:1.

A somewhat simpler structure is postulated for the monohydroxy quinone juglone of Example 1, this being

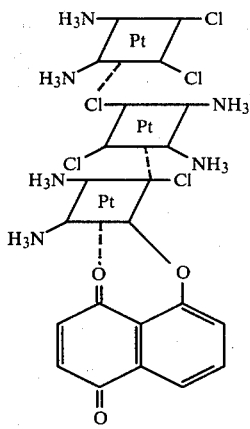

which displays a ratio of cis Pta₂Cl₂ to quinone of approximately 3:1.

In order to obtain the necessary product compositions, the molar charge proportions supplied to the ball-milling apparatus should be, in terms of Pt compound to quinone, 5:1 to 8:1 for dihydroxy quinones and 3:1 to 5:1 for monohydroxy quinones.

In addition to those cited in the examples, the following hydroxyquinones can be used to practice this invention: alizarin, 1,8 dihydroxy-9,10-anthraquinone, purpurin, daunomycin, carminomycin, 8,11-dihydroxy-5,12-naphthacenedione, 1,4-dihydroxy-5,8-bis[2-(hydroxyethyl) amino ethyl] amino-9,10-anthracenedione.

The following are typical examples of compounds prepared according to this invention, the platinum ingredient being dichlorodiammineplatinum (II), i.e., Pta₂Cl₂ or dichloro 1,2-cyclohexanediaminoplatinum (II),

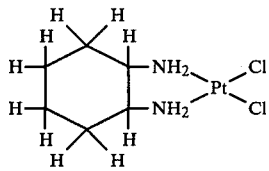

EXAMPLE 1

Preparation of juglone cis-Pta₂Cl₂ comples (I)
Juglone is a monohydroxy quinone having the structural formula:

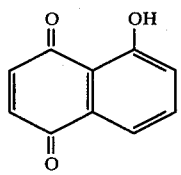

Into a 120 ml. ceramic jar containing approximately 70 g. of glass balls (5 mm. in diameter) and 40 ml of DMF was added 0.5 g cis-Pta₂Cl₂ and 0.074 g. juglone and the mixture ball-milled at room temperature (approximately 104 r.p.m. for a 3¼" outside diameter ball mill jar and approximately 170 r.p.m. for a 2" outside diameter ball mill jar) for 120 hours. At the conclusion of ball-milling the reaction mixture had an intense blue coloration.

The ball-milled suspension was filtered and the filtrate evaporated under approximately 10 mm. Hg vacuum to dryness. The residue was slurried in methylene chloride to remove unreacted juglone. The precipitate was collected on a frit-glass filter, redissolved in dimethyl formamide (10–15 ml.) and to the clear filtrate was added an excess of methylene chloride. The precipitate was collected and recrystallized as above to give 0.59 g. of complex I as a purple product.

The analysis calculated for $C_{10}H_{22}N_6Cl_6Pt_3O_3$ was C, 11.16%; H, 2.23%; N, 7.81%; Pt, 54.48%. The analysis actually found was C, 11.68%; H, 2.69%; N, 8.61%; Pt 55.51%. Absorption maxima (dimethyl formamide) was 270 and 380 nm. The ratio of cis-Pta₂Cl₂ to juglone is 3:1.

EXAMPLE 2

Preparation of 5,8-dihydroxy-2-methyl-1,4 napthoquinone cis-Pta₂Cl₂ complex (II). 5,8-dihydroxy-2-methyl-1,4 naphthoquinone has the structural formula:

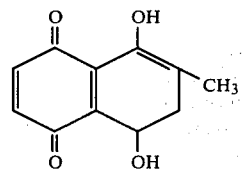

Following the procedure hereinbefore described for Example 1, 5,8 dihydroxy-2-methyl-1,4 naphthoquinone (0.085 g.) and cis-Pta₂ Cl₂ (0.50 g.) were condensed to give 0.43 g. of product II as purple crystals.

Analysis calculated for $C_{11}H_{38}N_{10}Pt_5O_4Cl_{10}$ was C, 7.76%; H, 2,25%; N, 8.23%; Pt, 57.23%. The analysis actually found was C, 7.65%; H, 3.08%; N, 7.30%; Pt, 56.31%. Absorption maxima in dimethylformamide was 270 mm., 410 nm.

The ratio of cis-Pta₂ Cl₂ to the quinone approximated 5:1.

EXAMPLE 3

Preparation of 1, 4 dihydroxy-9, 10-anthraquinone cis-Pta₂ Cl₂ complex (III).

1, 4-dihydroxy-9, 10-anthraquinone (quinizarin) has the structural formula:

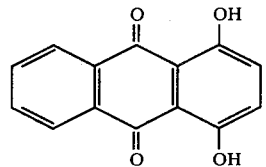

Following the procedure hereinbefore described for Example 1, 1, 4 dihydroxy-9, 10-anthraquinone (0.20 g.) was reacted with cis-Pta₂ Cl₂ (0.50 g.) to give 0.34 g. of product III as purple crystals.

Analysis calculated for $C_{14}H_{44}N_{12}Cl_{12}Pt_6O_4$ was C, 8.26%; H, 2.16%; Cl, 20.65%; Pt, 57.52%. The analysis actually found was C, 8.68%; H, 2.48%; Cl, 20.10%; Pt, 56.76%.

Absorption maxima in dimethylformamide are 275, 525, and 565 nm.

The ratio of cis-Pta$_2$ Cl$_2$ to quinizarin in the compound approximates 6:1.

EXAMPLE 4

Preparation of doxorubicin cis-Pta$_2$ Cl$_2$ complex (IV) Doxorubicin has the structural formula:

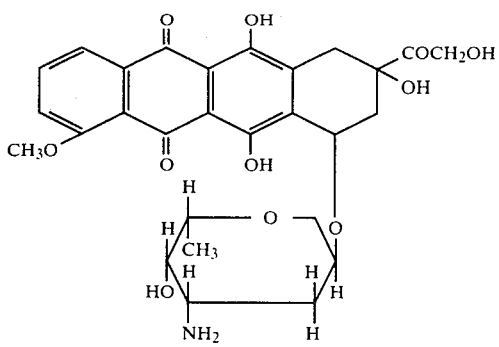

First, doxorubicin free base was prepared from doxorubicin hydrochloride.

Doxorubicin hydrochloride was converted to free base by bubbling gaseous ammonia through a capillary pipet into a stirred suspension of doxorubicin hydrochloride (0.050 g.) in 15 ml. of an 8:1 mixture of chloroform and methanol at 0° C. The bubbling of ammonia and the stirring were continued until the mixture was red-orange. After the ammonium chloride settled out overnight, the mixture was filtered and the filtrate, after dilution with 150 ml. of the same chloroform, methanol solvent supra, was heated at 60° C. for one hour to give a solution of 0.037 g. of doxorubicin base in 100 ml. of solvent.

Following the procedure hereinbefore described for Example 1, doxorubicin base (0.037 g.) and cis-Pta$_2$Cl$_2$ (0.104 g.) were condensed to give 0.103 g. of product IV as purple crystals.

Analysis calculated for C$_{27}$ H$_{65}$ O$_5$ N$_{11}$ Cl$_8$ Pt$_5$ was C, 15.85%; H, 2.89%; N, 7.53%; Pt, 47.70%. The analysis actually found was C, 15.99%; H, 3.19%; N, 7.65%; Pt, 47.62%. Absorption maxima in dimethylformamide was 475, 530, 575 nm.

The ratio of cis-Pta$_2$ Cl$_2$ to doxorubicin approximates 5:1.

EXAMPLE 5

Preparation of 5, 8-dihydroxy-1,4-naphthoquinone (naphthazarin) cis-Pta$_2$Cl$_2$ complex (V).

Following the procedure hereinbefore described for example 1, naphthazarin (0.0386 g.) and cis-Pta$_2$ Cl$_2$ (0.3673 g.) were condensed in 40 mlDMF to give 0.32 g. of recrystallized product (V) as dark blue crystals.

Absorption maxima in dimethylformamide was 301, 271, 606, 563.

EXAMPLE 6

Preparation of quinizarin cis-dichloro-1,2-cyclohexane diamino platinum II.

Following the procedure hereinbefore described for example 1, quinizarin (0.0447 g.) and cis-dichloro 1,2 diaminocyclohexane (0.3692 g.) were condensed in 40 ml. of DMF to give 0.30 g. of product VI as purple crystals.

Absorption maxima in dimethyl formamide was 303, 226, 565, 533.

Table I is a summary of the spectroscopic data identifying the several products of Example 1–6, inclusive.

TABLE I

| | | Ultraviolet Maxima (log $\epsilon$max) | | |
|---|---|---|---|---|
| | Example Number | Reagent maxima present in complex (nm) | Reagent maxima absent in complex (nm) | New maxima in complex only (nm) |
| cis Pt/Juglone complex | 1 | 270 | 425<br>370(w) | 485<br>380 |
| cis Pt/Naphthazarin complex | 5 | 301(sh)<br>271 | 546<br>510 | 606<br>563 |
| cis Pt/5,8-dihydroxy-2-methyl-1,4 naphthaquinone complex | 2 | 303(sh)<br>270(3.0) | 358<br>370(w) | 303(shoulder) |
| cis Pt/Quinizarin complex | 3 | 262 | 468<br>370(w) | 567(4.0)<br>525(4.1) |
| cis Pt/doxorubicin complex (IV) | 4 | 495<br>475 | 530 | 575 |
| cis diaminocyclohexane dichloro Pt(II)/Quinizarin complex | 6 | 303(sh)<br>266 | 468 | 565<br>533 |

| | Infrared Spectra Major Peaks (cm$^{-1}$) | | |
|---|---|---|---|
| Compound | Absorption cm$^{-1}$ | Assignment | Reference and Comments |
| cis Pt/Quinizarin complex<br>Example 3 | 3280<br>3200<br>2910<br>1650<br>1605 | $\nu$(NH$_3$)<br>$\nu$(NH$_3$)<br>Chelated OH<br>$\delta$ NH$_3$<br>C=O | 3<br>3<br>1<br>3<br>4, shifted to lower wavelength upon metal chelation |
| cis Pt/Doxorubicin complex<br>Example 4 | 3290<br>1750<br>1620–1650<br>1050–1150<br>780–790<br>610 | $\nu$(NH$_3$)<br><br>C=O<br>C—O—Pt<br> | 3<br><br><br>5<br> |

TABLE I-continued

| | 450 | Pt—O | 4 |
|---|---|---|---|

References
1. D. Hadzi, N. Sheppard, Trans. Far. Soc. 50, 911 (1954).
2. R. H. Thompson, Naturally Ocurring Quinones, Academic Press. pp. 39-92 (1971).
3. H. Poulet, et al., Spectrochim Acta 20, 1855 (1964).
4. K. Nakomoto, S. J. McCarthy, Spectroscopy and Structure of Metal Chelate Compounds, Wiley 268-276 (1968).
5. L. J. Bellamy, Infrared Spectroscopy of Complex Molecules, Wiley (1959).

Table II is a summary of the results of in vivo testing of typical products according to this invention. These experiments were performed in the standard assay of the Ascites Sarcoma 180 in the ICR mice. There were six mice in each cage, with two cages for the negative controls, two cages for the positive controls and one cage for each dose level of drug tested. Tumor cell injections of about $10^6$ cells were performed on Day 0 and drug injection Day 1, both given intraperitoneally (IP). Metal coordination compounds were suspended in normal saline as a carrier.

The results of the in vivo tests performed on mice with two of the compounds can be seen from Table II. These tests confirm the synergistic action of the coordination compounds. Some doses were significantly better than the positive control (7 mg/kg single injection of cis-Pta$_2$Cl$_2$). The improvement in the life span compared to the positive control is substantial. Larger doses of coordination compound over positive control with reduced toxicity can be tolerated.

TABLE II
In vivo test results

| Compound | Dose mg. compound/kg mouse | Average day of death | % Increased life span | No. of Cures (out of 6) |
|---|---|---|---|---|
| negative control | 0 | 17.3 | — | — |
| positive control 7mg/kg cis Pta$_2$ Cl$_2$ | 0 | 31.3 | 80 | 4 |
| cis-Pt/Doxo compound Example 4 | 5 | 34.2 | 97 | 4 |
| | 10 | 36.0 | 108 | 6 |
| | 15 | 34.8 | 101 | 1 |
| | 20 | 26.2 | 51 | 1 |
| negative control | 0 | 13.8 | — | — |
| positive control 7mg/kg cis-Pta$_2$ Cl$_2$ | 0 | 25 | 81 | 1 |
| cis-Pt/Quiniz. Example 3 | 8 | 28 | 107 | 1 |
| | 12.5 | 26 | 88 | 0 |
| | 25 | 16.0 | 16 | 0 |
| | 50 | 2.75 | −80 | |
| | 100 | 3.8 | −72 | |

What is claimed is:

1. A metal coordination compound comprising, as a therapeutic portion,
   (a) A multi-ring quinone having at least one hydroxy group in a ring fused to the quinone ring as ligand,
   (b) chelated at keto and hydroxy groups with the platinum metal
   (c) in a cis-dichloro platinum (II) compound having two platinum metal coordinate bonds each joined to a member of the group consisting of ammonia, mono-substituted ammonia and ammonia radicals connected one to the other by single valence bonds through adjacent carbons of a carbon ring compound, and
   (d) additional cis-dichloro platinum (II) compound not bonded to the hydroxy quinone but coordinated to said platinum which is bonded to said hydroxy quinone, and, as a non-therapeutic portion,
   (e) excess platinum in the form of tetrachloro-platinate anion.

2. A metal coordination compound according to claim 1 wherein said multi-ring quinone is doxorubicin and said cis-dichloro platinum (II) compound is cis-dichlorodiammine platinum (II).

3. A metal coordination compound according to claim 1 wherein said cis-dichloro platinum (II) compound is cis-dichloro 1, 2 -cyclohexane diamino platinum (II).

4. A metal coordination compound according to claim 1 wherein said cis-dichloro (II) compound has the general formula cis (RNH$_2$)$_2$ dichloro platinum (II) wherein R can be hydrogen or an alkyl group having 1 to 10 carbon atoms.

5. A metal coordination compound according to claim 4 wherein said cis-dichloro platinum (II) compound is cis.

6. A metal coordination compound according to claim 1 wherein said multi-ring quinone is a member of the group juglone, naphthazarin quinizarin, alizarin, and 8, 11 dihydroxy 5, 12 naphthacenedione.

7. The method of manufacturing a metal coordination compound of the composition of claim 1 comprising, in the sequence recited, mixing said multi-ring quinone with said cis-dichloro platinum II in a liquid heat sink comprising essentially a solvent for one of the reactants, ball milling said mixture with said liquid heat sink at room temperature in a hermetically sealed ceramic or glass jar for at least 12 hours using glass, ceramic or other non-metallic balls, filtering solids from said liquid heat sink and from the filtrate to recover said metal coordination compound.

8. The method of manufacturing a metal coordination compound according to claim 8 wherein said solvent is a member of the group dimethyl formamide, dimethyl acetamide, methylene chloride, methyl pyrolidone, hexamethyl phosphoramide.

9. The method of manufacturing a metal coordination compound according to claim 7 wherein said cis-dichloro platinum (II) compound is proportioned to said quinones as charged in the ratios of approximately 5:1 to 8:1 in mols for quinones having two hydroxy groups and approximately 3:1 to 5:1 in mols for quinones having one hydroxy group.

* * * * *

UNITED STATES PATENT AND TRADEMARK OFFICE
CERTIFICATE OF CORRECTION

PATENT NO. : 4,283,342
DATED : August 11, 1981
INVENTOR(S) : Seymour Yolles

Page 1 of 2

It is certified that error appears in the above-identified patent and that said Letters Patent are hereby corrected as shown below:

Col. 3, lines 57-67

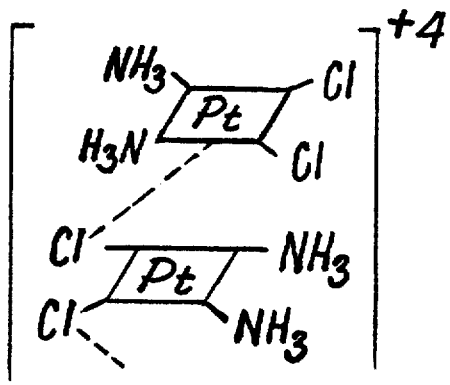

Col. 4, lines 36-44

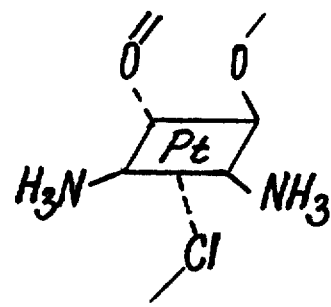

Col. 4, lines 14-33

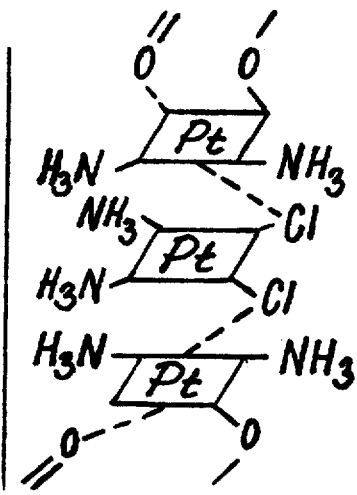

Col. 5, lines 5-13

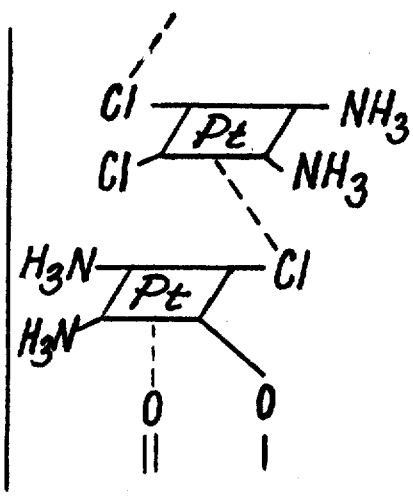

UNITED STATES PATENT AND TRADEMARK OFFICE
CERTIFICATE OF CORRECTION

PATENT NO. : 4,283,342
DATED : August 11, 1981
INVENTOR(S) : Seymour Yolles

It is certified that error appears in the above—identified patent and that said Letters Patent is hereby corrected as shown below:

Col. 6, line 41 - "270mm" should read --270nm.--

Col. 8, line 34 - "226" should read --266--

Col. 10, line 34 - After "cis" add --[bis(isopropylamino)dichloro platinum (II)]

Col. 10, line 44 - After "said mixture" insert --of ingredients--

Col. 10, line 51 - "claim 8" should read --claim 7--

Signed and Sealed this

Sixteenth Day of March 1982

[SEAL]

Attest:

GERALD J. MOSSINGHOFF

Attesting Officer        Commissioner of Patents and Trademarks